United States Patent [19]

Moore

[11] Plant 4,496

[45] Jan. 22, 1980

[54] MINIATURE ROSE PLANT

[76] Inventor: Ralph S. Moore, 2519 East Noble Ave., Visalia, Calif. 93277

[21] Appl. No.: 968,477

[22] Filed: Dec. 11, 1978

[51] Int. Cl.[2] ..... A01H 5/00
[52] U.S. Cl. ..... Plt./7
[58] Field of Search ..... Plt./7

*Primary Examiner*—Robert E. Bagwill

[57] ABSTRACT

The subject of the present disclosure is a new and distinct variety of miniature rose plant characterized primarily by the rich orange color of buds and flowers and further identified by the change and blending of deeper orange and red shades in the flowers as they mature outdoors, especailly in cool weather.

8 Drawing Figures

The present invention relates to a new and distinct variety of hardy, dwarf, bush type rose plant of the miniature class; the variety being primarily characterized—as to novelty—by rich orange buds and flowers which in general color effect are similar to Marigold Orange 11/2 (when grown in greenhouse).

The variety is further characterized by:

An abundance of bloom, with flowers borne singly or several to the stem in loose clusters.

Fruity sweet fragrance.

A plant which is vigorous, of rounded somewhat spreading shape with semi-glossy (to matt) small foliage with pointed leaflets; the buds and flowers being similar in form and size to Over the Rainbow (miniature—U.S. Plant Pat. No. 3,472).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Rumba, a Floribunda (U.S. Plant Pat. No. 1,919, expired) as the seed parent and Over the Rainbow, miniature, (U.S. Plant Pat. No. 3,472), as the pollen parent.

Subsequent to origination of the variety I successfully asexually reproduced it at Sequoia Nursery, located as aforesaid, by budding as well as by cuttings; the reproductions having run true in all respects.

The color photographs illustrate the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

Variety name: Orange Honey.

Flowers borne: several together (3 to 5) but usually singly on slender, wirey stems.

Quantity of bloom: abundant both outside and in greenhouse.

Bud:

*Peduncle.*—Medium to long; slender but sturdy; erect; medium to light green; hairs — numerous short hairs.

*Before calyx breaks.*—Size — small. Form long: pointed with numerous soft, very short hairs and several foliaceous appendages on surface of bud; with foliaceous parts extending beyond the tip of the bud equal to one-half or more of its length. Color — medium green.

*As calyx breaks.*—Color — medium yellow — near Cadmium Orange 8/2, becoming near Saffron Yellow 7/2 toward base. Opening: opens well in all weather.

Bloom:

*Size when fully open.*—Small, averaging about 35 mm (1¼").

*Petalage.*—Semi-double — averaging about 18–20 petals, arranged regularly plus sometimes several petaloids.

*Form.*—High centered to cupped at first, becoming more open, with petals rolled loosely outward, and later at maturity open with petals remaining in similar shape and position. Open flowers show stamens.

Petals: Fairly thick; satiny on inside and on outside surface.

*Shape.*—Outside petals, broad lanceolate (nearly round) with very short acute tip; intermediate — broad lanceolate, rounded with very small acute tip; inside — lanceolate with acute or rounded tip.

Color: Newly opened flower from a plant grown in plastic greenhouse:

*Outside petal.*—Outside surface — yellow at base, near Cadmium Orange 8/2, blending into a shade or shades of orange near Orpiment Orange 10 or Marigold Orange 11/1. Inside surface — near Maize Yellow 607 on basal ½ to ⅓ of petal, then changing into orange of a shade (or shades) which may vary in intensity from Marigold Orange 11/1 to Orange 12 and outdoors in cooler weather may be near Saturn Red 13/1. Note: From flowers outdoors (late fall — cool weather): Outside petal: Outside surface — near Orpiment Orange 10/2 splashed or overlaid with red, near Geranium Lake 20/1 but may be lighter or darker shade(s). Inside surface — near Cadmium Orange 8/1 on lower ⅓ of petal changing to a color near Poppy Red 16/1 on tip ⅔ of petal. Intermediate and inner petals similar to outside petals but less red.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers—color bright orange. Three days open—color similar to newly opened flowers (A) in greenhouse, after several days, the color ages lighter tending to become more pink; (B) outdoors, color tends to become more red, with a general color effect similar to Circus (Floribunda, U.S. Plant Pat. No. 1,382, expired). Behavior — opens well in all weather. Spent petals drop off. Flower longevity (May 1978) — plant in pot 6–8 days. Cut flowers at living room temperature 5–7 days.

Reproductive Organs:

*Stamens.*—Abundant, arranged regularly about pistils.

*Filaments.*—Varying length, medium to long, yellow.

*Anthers.*—Well formed; yellow.

*Pollen.*—Abundant amount.

*Pistils.*—Average number.

*Styles.*—Fairly even; medium length; bunched; color — pale greenish.

*Stigmas.*—Pale greenish.

*Ovaries.*—All enclosed in calyx.

*Hips.*—Some.

*Sepals.*—Permanent; spear shaped; recurved.

*Seed.*—Several.

Foliage:

*Leaves.*—Compound of five leaflets. Size — small; leathery; semi-glossy to matt.

*Leaflets.*—Shape: broad lanceolate; eliptical; apex acute; base rounded or rounded acute. Margin serrate. Color: Medium green; new growth — normal (medium) green, sometimes reddish or bronze (outdoors). Rachis: medium strength; upper side may have a few tiny short hairs or prickles, grooved, underside few small hooked thorns and usually no hairs and tiny prickles. Stipules: medium long; narrow to medium width; short length narrow points which turn out usually at about 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Average; slender; straight, inclined slightly downward; color; dark brown. Prickles — few or none; hairs — none.

*Branches.*—Color: light to medium green. Thorns: average; medium length; slender; nearly straight, inclined slightly downward. Medium to short oval base. Prickles: few or none. Hairs: some.

*Young shoots.*—Color: light to medium green (reddish outdoors). Thorns: average, slender; straight, inclined slightly downward; color — greenish (or bronzy).

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit substantially as illustrated and described characterized by buds and flowers which are (1) clear orange in color, with sometimes darker shading, the buds and flowers resembling Over the Rainbow (miniature—U.S. Plant Pat. No. 3,472) in size and shape and (2) as grown outdoors in cool weather the orange coloring of bud and flower being overlaid or blended with varying shades of red to give a multicolor effect similar to the Floribunda rose Circus (U.S. Plant Pat. No. 1,382, expired); and further characterized by a plant which is vigorous and compact, easy to propagate from soft wood cuttings or by budding, with an abundance of flowers borne singly or several to the stem in loose clusters.

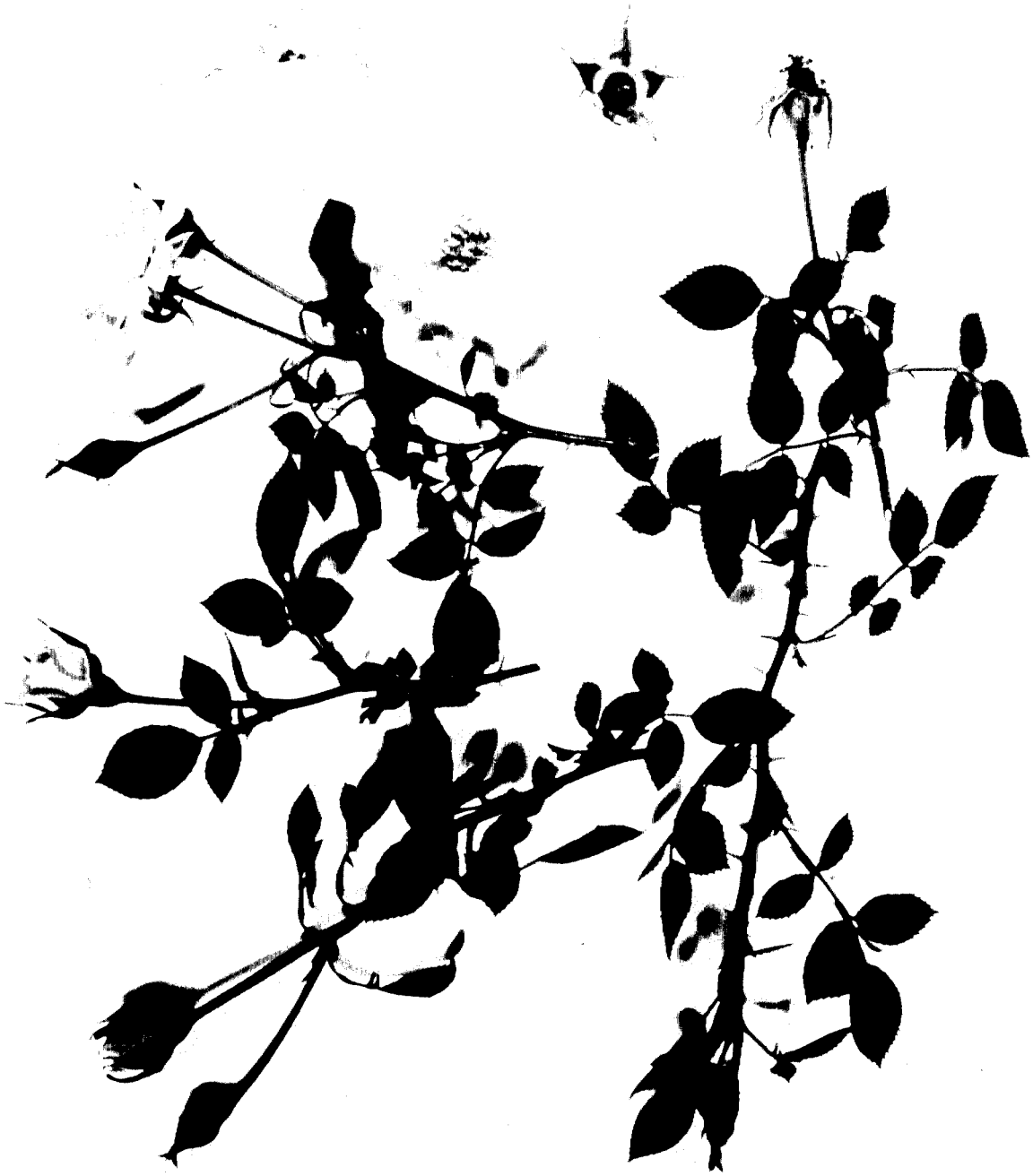

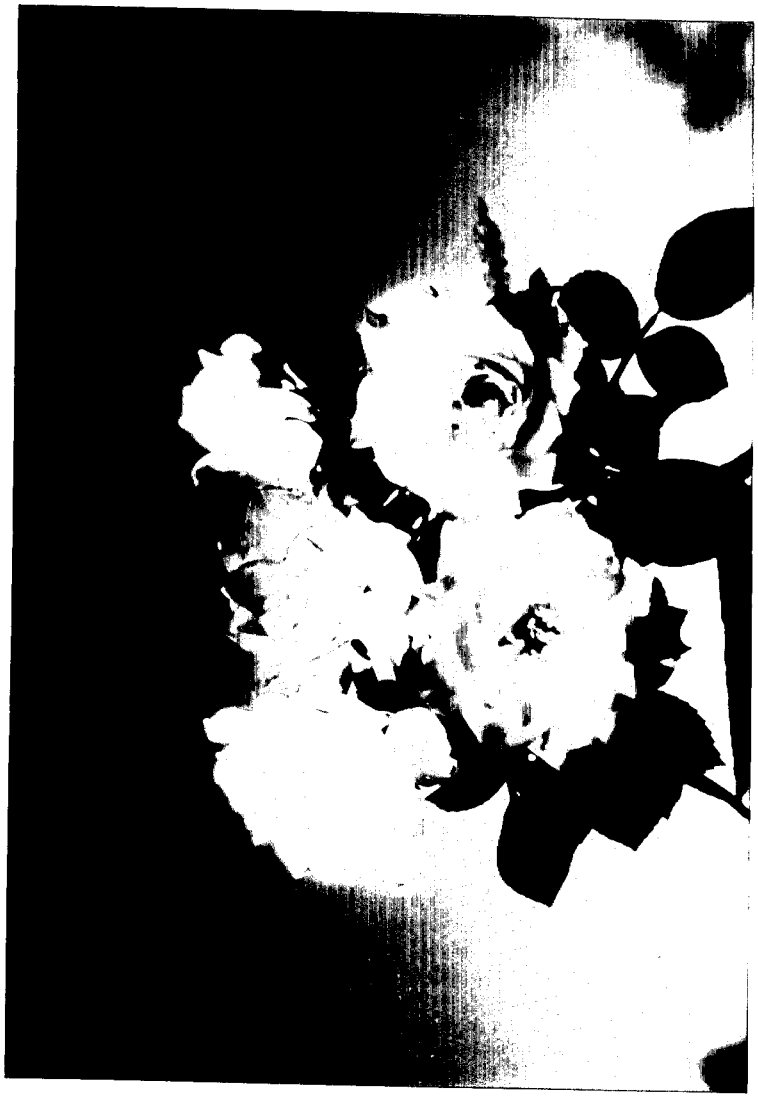

* * * * *